US012376913B2

(12) United States Patent
Boddington et al.

(10) Patent No.: US 12,376,913 B2
(45) Date of Patent: Aug. 5, 2025

(54) THREE-DIMENSIONAL DUAL FIDUCIAL-SENSOR TRACKABLE DEVICE AND METHOD OF USE

(71) Applicant: ORTHOGRID SYSTEMS, INC., Millcreek, UT (US)

(72) Inventors: Richard Boddington, Salt Lake City, UT (US); Vincent Agnus, Illkirch (FR); Edouard Saget, Boise, ID (US); Erik Noble Kubiak, Las Vegas, NV (US)

(73) Assignee: Orthogrid Systems, Inc., Millcreek, UT (US)

( * ) Notice: Subject to any disclaimer, the term of this patent is extended or adjusted under 35 U.S.C. 154(b) by 160 days.

(21) Appl. No.: 18/139,471

(22) Filed: Apr. 26, 2023

(65) Prior Publication Data
US 2024/0130797 A1 Apr. 25, 2024
US 2024/0225744 A9 Jul. 11, 2024

Related U.S. Application Data

(60) Provisional application No. 63/335,271, filed on Apr. 27, 2022.

(51) Int. Cl.
*A61B 34/20* (2016.01)
*A61B 34/10* (2016.01)
*A61B 90/00* (2016.01)

(52) U.S. Cl.
CPC .............. *A61B 34/20* (2016.02); *A61B 34/10* (2016.02); *A61B 90/36* (2016.02); *A61B 90/39* (2016.02); *A61B 2034/102* (2016.02); *A61B 2034/107* (2016.02); *A61B 2034/2048* (2016.02); *A61B 2034/2055* (2016.02); *A61B 2090/363* (2016.02); *A61B 2090/367* (2016.02);
(Continued)

(58) Field of Classification Search
CPC ......... A61B 34/20; A61B 34/10; A61B 34/25; A61B 90/36; A61B 90/39; A61B 2034/102; A61B 2034/107; A61B 2034/2048; A61B 2034/2055; A61B 2034/2051; A61B 2034/2065; A61B 2090/393; A61B 2090/367; A61B 2090/3966; A61B 2090/3983
See application file for complete search history.

(56) References Cited

U.S. PATENT DOCUMENTS

| 6,464,723 | B1 * | 10/2002 | Callol ................. A61F 2/91 623/1.34 |
| 10,463,435 | B2 | 11/2019 | Saget et al. |
| 2020/0205900 | A1 | 7/2020 | Buckland et al. |

(Continued)

*Primary Examiner* — Peter Luong
(74) *Attorney, Agent, or Firm* — SCHWEGMAN LUNDBERG & WOESSNER, P.A.

(57) ABSTRACT

The subject of this invention is a surgical instrument positioning system using a three-dimensional dual fiducial-sensor trackable device and a method of intra-operative use of the three-dimensional dual fiducial-sensor trackable device for joint replacement, spine, hip, trauma fracture reduction, and implant placement/alignment. The surgical instrument positioning system provides real time position of a surgical device with reference to the three-dimensional dual fiducial-sensor trackable device using a fluoroscopic image. The three-dimensional dual trackable device is enabled to receive at least one of K-wire, guide wire, fixation rod, drill bit, screw, and surgical device.

19 Claims, 13 Drawing Sheets

(52) U.S. Cl.
CPC ............... *A61B 2090/3966* (2016.02); *A61B 2090/3983* (2016.02)

(56) References Cited

U.S. PATENT DOCUMENTS

2020/0323649 A1   10/2020   Schipper et al.
2021/0321877 A1*  10/2021   Fields ................... A61B 90/39

\* cited by examiner

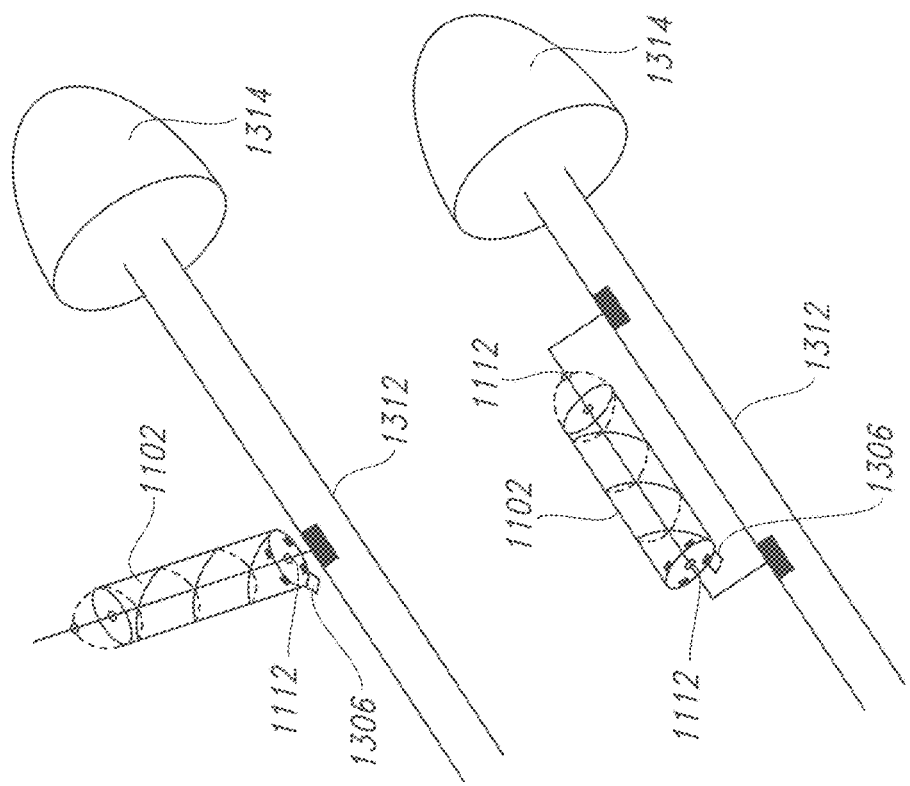
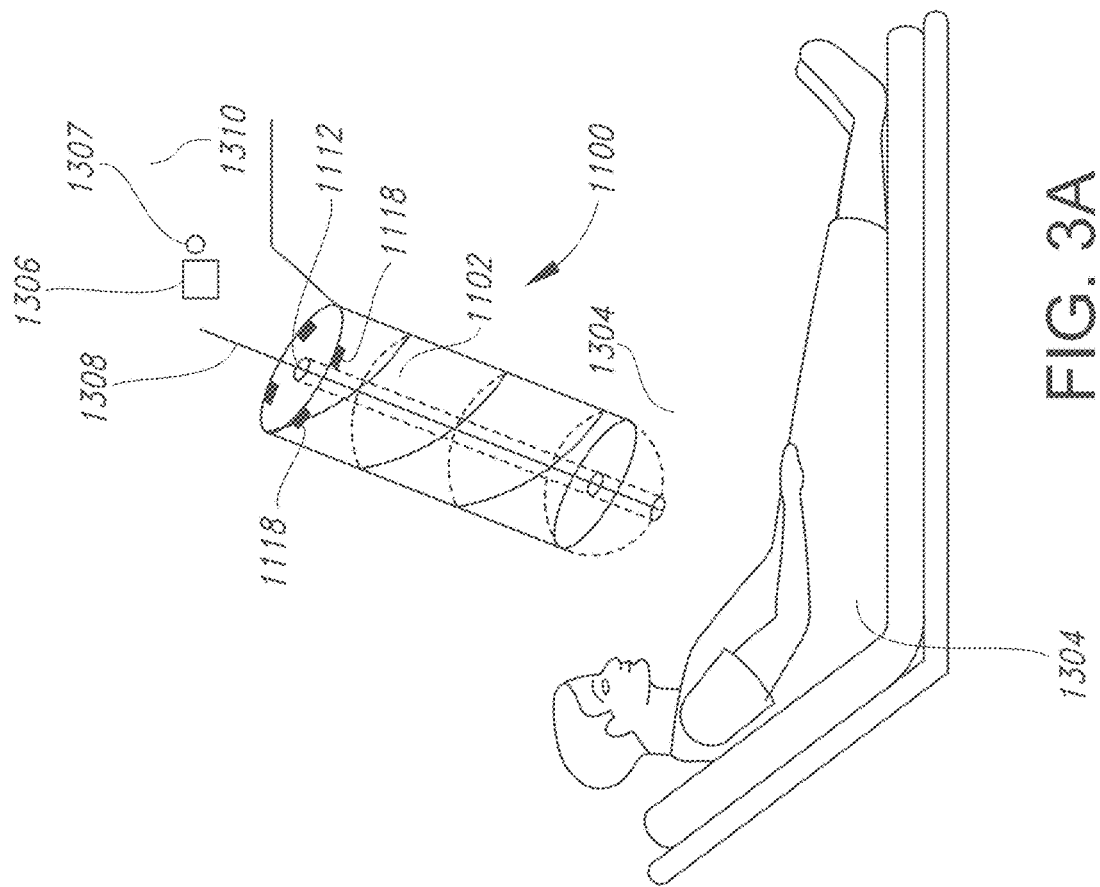

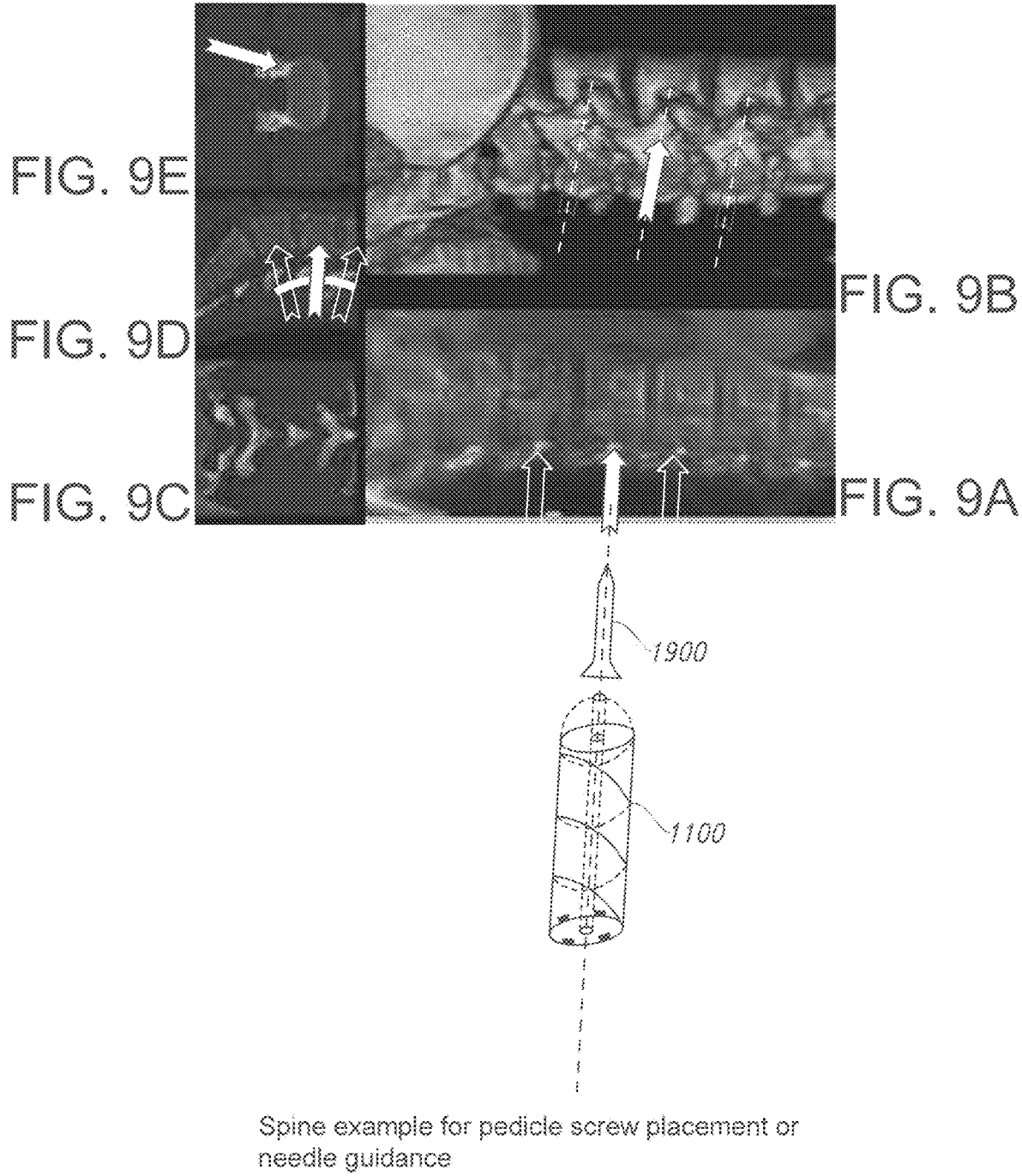
Spine example for pedicle screw placement or needle guidance

Trauma Plate & Screw example for Ankle

Trauma Plate & Screw example for Ankle

Shoulder Implant example showing glenoid guidance

Shoulder Implant example showing glenoid guidance

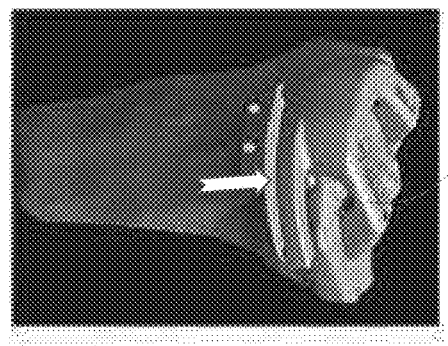
FIG. 12A
Knee Implant example showing guidance of cutting guides/blocks.
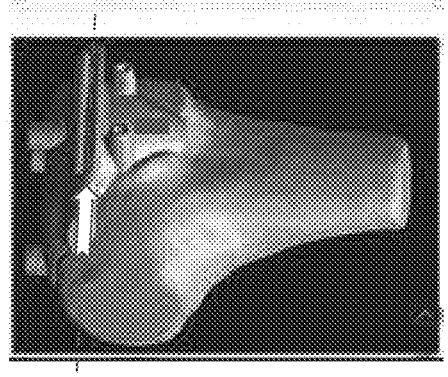
FIG. 12B
Knee Implant example showing guidance of cutting guides/blocks.
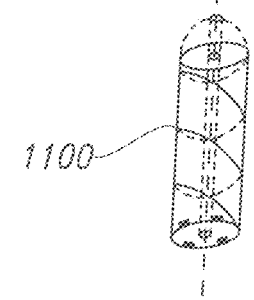
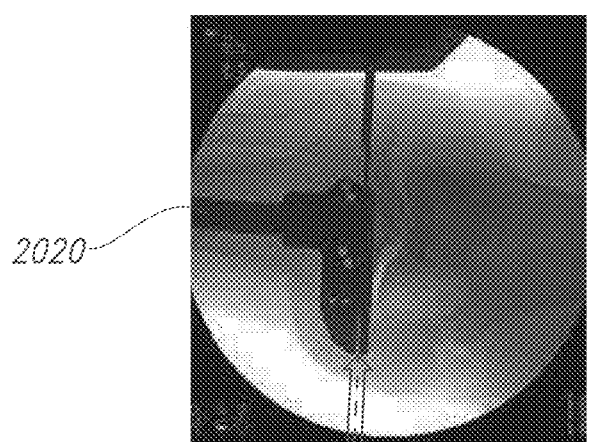
FIG. 12C
Knee Implant example showing guidance of cutting guides/blocks.
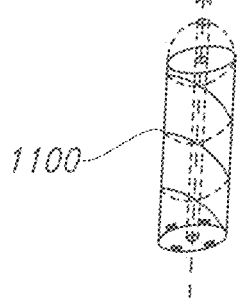

THREE-DIMENSIONAL DUAL FIDUCIAL-SENSOR TRACKABLE DEVICE AND METHOD OF USE

FIELD OF THE INVENTION

The subject of this invention is a surgical instrument positioning system using a three-dimensional dual fiducial-sensor trackable device and a method of intra-operative use of the three-dimensional dual fiducial-sensor trackable device for joint replacement, spine, hip, trauma fracture reduction, sport medicine, implant placement/alignment and pain management. The duality of the three-dimensional tracking is ensured by the simultaneous dual localizable in the fluoroscopic images and an inertial sensor.

BACKGROUND OF THE INVENTION

Currently for guiding a surgeon during intra-operative implant placement a fluoroscopic image and image-guided surgery (IGS) is used. The image-guided surgery (IGS) uses optical camera tracking (LED's/Infrared) of reference attached to a patient's body or surgical instrument. Alternatively, the surgeon can perform an open procedure (i.e., large incision) and eyeball the implant placement. The eyeball method requires a large incision and is not suitable for minimally invasive surgery. Current fluoroscopy approach relies on the surgeon to interpret patient's information visually and manually on the fluoroscopy image to determine a location for an optimal placement of the implant. The surgeon is enabled to manually measure the patient's anatomical structure and relative geometry of the implant location that leads to error in placement or low accuracy of the implant placement. Also, the surgeon requires continuous antero-posterior (AP) and lateral imagery of the patient that leads to high level of radiation exposure to the patient.

The image-guided surgery (IGS) approach uses optical markers that are placed on the patient, wherein the optical markers are tracked via a camera to estimate their three-dimensional location with reference to the patient's anatomical structure. Further, to preserve spatial coherence when the patient is moving during surgery, the optical markers are needed to be statically fixed on the patient's body. The fixation of the optical markers on the patient's body requires an incision and drilling into the healthy bones of the patient using long screws. This process involves a high risk of infection. Further, to locate the patient's anatomical structure, the surgeon manually points to the patient's anatomical structure using a probe that comprises optical markers. Therefore, the patient's anatomical structure is sometimes poorly defined (due to smooth contours of the bones) that leads to a lot of error in the image-guided surgery or computer-assisted surgery. Further, the optical markers sometimes hide certain patient anatomical structures in the fluoroscopic image. Further, the shape of the optical marker limits freedom of maneuver during surgery to avoid collisions and occlusions. Also, the placement of the optical markers needs a lot of time. The optical tracking system only relies on the camera and the relative position to the reference marker. There is no relationship with fluoroscopy.

Therefore, there is need for a radio-opaque marker enabled to guide the surgeon for the implant placement via a single fluoroscopic image to reduce intra-op radiation, cost, and time of the surgery. This novel approach avoids the use of multiple fluoroscopic images and provides a more efficient and error-free approach. Further, a radiographic image enables the surgeon to intra-operatively view anatomy, surgical instrument, and implant location.

SUMMARY OF THE INVENTION

The inventive subject matter includes a three-dimensional dual fiducial-sensor trackable device made of a cylindrical element having a first end and a second end, wherein the first end has a first radio-opaque disk disposed therein, wherein the second end has a second radio-opaque disk disposed therein. The first radio-opaque disk and the second radio-opaque disk determine two or three-dimensional positioning of the cylindrical element in a fluoroscopic image. The cylindrical element has a hollow slot in between the first end and the second end, wherein the hollow slot is configured to receive a surgical element. The surgical element is at least one of the but not limited to a K-wire, guidewire, fixation rod, and surgical device. Further, the cylindrical element has a radio-opaque wire attached along a surface area of the cylindrical element; wherein the radio-opaque wire determines a pose or position of the cylindrical element in the fluoroscopic image. Further, a sensor such as an inertial measurement unit is coupled to the second end of the cylindrical element. The inertial measurement unit is configured to transmit one or more parameters to a display unit through a wireless network, wherein the one or more parameters are a position, an angle, acceleration, x, y, z coordinates of the inertial measurement unit. The inertial measurement unit is made of an accelerometer, a NEMS gyrometer, or a gyroscope.

The inventive subject further includes a method for intra-operative use of an at least one three-dimensional dual fiducial-sensor trackable device for intraoperative navigating a surgical device or anatomical structure. The method includes the steps of: placing the at least one three-dimensional dual fiducial-sensor trackable device on to a portion of patient's anatomy, or attaching the device to an instrument, an implant, or an imaging device, wherein each of the at least one three-dimensional dual fiducial-sensor trackable device is made of a distinct radio-opaque pattern and an inertial measurement unit; capturing a fluoroscopic image of the patient's anatomy using an imaging device; intraoperatively determining a first positioning data of the distinct radio-opaque pattern on the fluoroscopic image; obtaining a second positioning data of the inertial measurement unit; overlaying the first positioning data and the second positioning data of the inertial measurement unit to determine a real time position of the patient anatomy, the instrument, the implant, or the imaging device in the fluoroscopic image; determining a position of the portion of the patient anatomy, the instrument, the implant, or the imaging device, with reference to the real time position of the at least one three-dimensional dual fiducial-sensor trackable device; and displaying a real time graphical representation of the least one three-dimensional dual fiducial-sensor trackable device on the fluoroscopic image relative to the portion of the patient anatomy, the instrument, the implant, or the imaging device This method can further include the step of: intraoperatively navigating the surgical device with reference to a real time graphical representation of the at least one three-dimensional dual fiducial-sensor trackable device.

In an exemplary embodiment, the method is configured for providing an angle between the patient's anatomy and the real time position of the cylindrical element. The positioning data of the cylindrical element is the position and orientation of the cylindrical element in the fluoroscopic image with reference to the patient's anatomy. The method is configured to, from the pose estimation of the cylindrical element within the fluoroscopic image and the positioning data of the inertial measurement unit during the same fluoroscopic image, determine the real-time new spatial position of the three-dimensional dual fiducial-sensor trackable device when the surgeon moves an instrument, implant, bone, or surgical device in space.

The present subject matter includes a method for intra-operative use of a three-dimensional dual fiducial-sensor trackable device for navigating a surgical device, the method includes the steps of immobilizing (temporarily during the fluoroscopic acquisition or attach to patient) the three-dimensional dual fiducial-sensor trackable device relative to a patient's anatomy, wherein the three-dimensional dual fiducial-sensor trackable device includes a cylindrical element, and an inertial measurement unit, wherein the cylindrical element, having a hollow slot along its length and configured to receive a surgical device, capturing a fluoroscopic image of the patient using an imaging device, determining a positioning data of the cylindrical element on the fluoroscopic image using a first radio-opaque disk, a second radio-opaque disk, and a radio-opaque wire of the cylindrical element, obtaining a positioning data of the inertial measurement unit, overlaying the positioning data of the cylindrical element and the positioning data of the inertial measurement unit to determine real time position of the cylindrical element on the fluoroscopic image, determining position of the surgical device with reference to the real time position of the cylindrical element and the patient's anatomy, displaying a real time graphical representation of the cylindrical element and the trajectory of its principal axis on the fluoroscopic image relative to the surgical device and the patient's anatomy and intra-operatively navigating the surgical device with reference to the real time graphical representation the cylindrical element and the trajectory of its principal axis.

In an embodiment, the method is configured for providing an angle between the patient's anatomy and the real time position of the cylindrical element. The positioning data of the cylindrical element is the position and orientation of the cylindrical element in the fluoroscopic image with reference to the patient's anatomy. The positioning data of the inertial measurement unit is a position, x, y, and z coordinates, angle, or orientation of the inertial measurement unit. The method is configured for overlaying the positioning data of the cylindrical element and the positioning data of the inertial measurement unit to determine the real-time position of the cylindrical element on the fluoroscopic image including the step of overlaying a two-dimensional positioning data of the cylindrical element and a three-dimensional positioning data of the inertial measurement unit on the fluoroscopic image.

BRIEF DESCRIPTION OF THE SEVERAL VIEWS OF THE DRAWING

FIG. 3A-3C is a schematic diagram showing the three-dimensional dual fiducial-sensor trackable device of this invention with different mounting configurations.

FIG. 7A-7C is an illustrative embodiment showing the three-dimensional dual fiducial-sensor trackable device coupled to a cup impactor.

FIG. 9A-9E is an illustration of the use of the present device for treatment of a spine for pedicle screw placement or needle guidance.

FIG. 12A-12C is an illustration of the use of the present device for a knee implant using cutting guides and blocks.

DETAILED DESCRIPTION OF THE INVENTION

Figure 1:
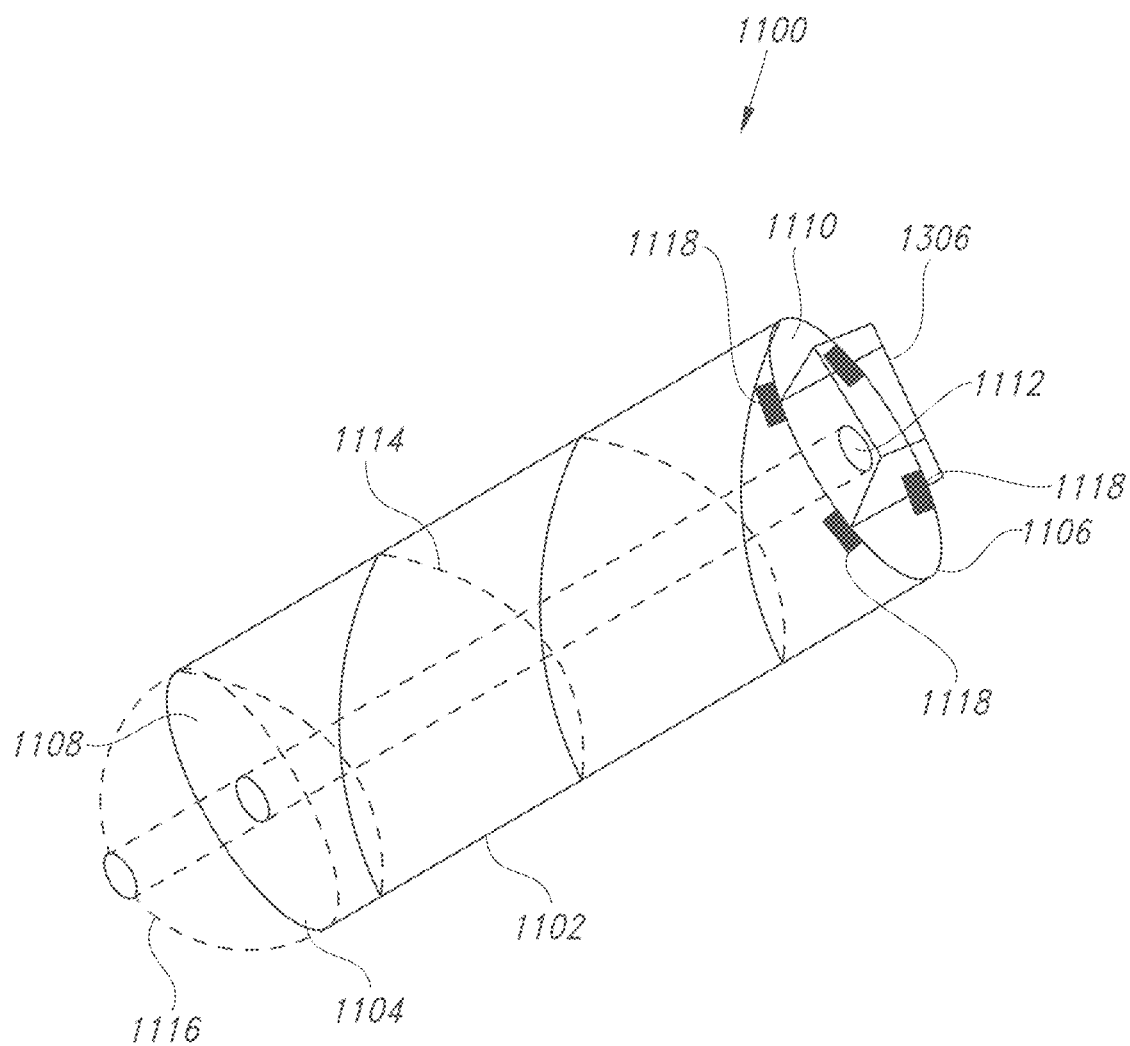
FIG. 1 is a schematic diagram of a cylindrical element of a three-dimensional dual fiducial-sensor trackable device.

The present invention may be understood more readily by reference to the following detailed description of the invention. It is to be understood that this invention is not limited to the specific devices, methods, conditions, or parameters described herein, and that the terminology used herein is for describing embodiments by way of example only and is not intended to be limiting of the claimed invention. Also, as used in the specification including the appended claims, the singular forms "a," "an," and "the" include the plural, and reference to a numerical value includes at least that value, unless the context clearly dictates otherwise. Ranges may be expressed herein as from "about" or "approximately" one value and/or to "about" or "approximately" another value. When such a range is expressed, another embodiment includes from the one value and/or to the other value. Similarly, when values are expressed as approximations, by use of the antecedent "about," it will be understood that the value forms another embodiment.

These and other aspects, features and advantages of the invention will be understood with reference to the detailed description herein and will be realized by means of the various elements and combinations particularly pointed out in the appended claims. It is to be understood that both the foregoing general description and the following detailed description of the invention are exemplary and explanatory of preferred embodiments of the inventions and are not restrictive of the invention as claimed. Unless defined otherwise, all technical and scientific terms used herein have the same meaning as commonly understood by one of ordinary skill in the art to which this invention belongs.

The present invention provides a dual fiducial-sensor three-dimensional trackable device that can be simultaneously tracked using a single fluoroscopic image, and in space due to an inertial measurement unit. A fiducial is a marker that is placed in the field of view of an imaging system. The purpose of a dual fiducial-sensor three-dimensional trackable device is to provide in real time, a virtual representation of its new localization into a fluoroscopic image without the need to acquire a new one. Hence, it could be used to guide surgeon gesture or hand during orthopedic procedures to provide an error free implant placement using a fluoroscopic image. In an exemplary embodiment, the three-dimensional dual fiducial-sensor trackable device is placed relative to a patient's anatomical structure to triangulate real time position of an anatomical feature/structure relative to the surgical device and radiographic image. The three-dimensional dual fiducial-sensor trackable device can be placed or attached to a surgical instrument, patient's body, implant, or a robot arm. In operation, dual fiducial-sensor three-dimensional trackable device provides guidance to a user such as a surgeon in positioning or tracking a surgical device, such a surgical instrument, during intra-operative use of this instrument on a patient for joint replacements, spine, sports medicine, pain management, trauma fracture reductions, deformity correction and implant placement/alignment. The three-dimensional dual fiducial-sensor trackable device is designed to be reusable and can be wrapped in a sterile bag when not in use.

Now referring to FIG. 1 a schematic diagram of a three-dimensional dual tracking device 1100 is provided. Element 1102 is configured to be tracked in real-time during orthopedic surgery and to provide image free guidance. The three-dimensional dual tracking device 1100 includes element 1102 shown in an exemplary form as a cylinder. The cylindrical element 1102 may be made of a biomaterial and can be covered with rubber to force the surgical element to remain in place or centered when inserted into the hollow slot 1112. The cylindrical element 1102 has a hollow slot 1112 disposed between the first end 1104 and the second end 1106, wherein the hollow slot 1112 has a diameter of about 2 mm in this exemplary embodiment. The hollow slot 1112 is configured to receive a surgical element such as a K-wire, a fixation rod, drill bit, screw or a surgical device. In this exemplary embodiment, the cylindrical element 1102 has a diameter of about 15 mm and a length of about 5 cm and is not radiopaque.

The cylindrical element 1102 has a first end 1104 and a second end 1106 disposed therein. The first end 1104 has a first radio-opaque disk 1108 attached therein and the second end 1106 having a second radio-opaque disk 1110 attached therein. In this exemplary embodiment, the first radio-opaque disk 1108 and the second radio-opaque disk 1110 have a thickness of about 0.5 mm. The first radio-opaque disk 1108 and the second radio-opaque disk 1110 are configured to determine two or three-dimensional positioning of the cylindrical element 1102 in a fluoroscopic image. The first end 1104 of the cylindrical element 1102 is a round-shaped end 1116 that enables to rotate the cylindrical element 1102 when in contact with a user's bone or user's skin (i.e., when the three-dimensional dual fiducial-sensor trackable device is in contact with a patient's body).

The first end 1104 of the cylindrical element 1102, in an exemplary embodiment, is of a generally rounded-shaped end and it rotates the cylindrical element 1102 when in contact with a patient's bone or patient's skin (i.e., when the three-dimensional dual fiducial-sensor trackable device is attached to a patient's body). Further, the cylindrical element 1102 has a radio-opaque wire 1114 disposed along a surface area of the cylindrical element 1102, wherein the radio-opaque wire 1114 enables a determination of the pose or the position (relative from C-Arm Image Intensifier) of the cylindrical element 1102 from the analysis of the fluoroscopic image. The position are the three dimensional coordinates (x,y,z) and the pose are the three rotational angles of an object. These positions and angles are the coordinates in relation to the C-ARM reference frame (i.e., the image intensifier) so the relative position/position between them is known.

Further, an inertial measurement unit 1306 is coupled to the second end 1106 of the cylindrical element 1102. The inertial measurement unit 1306 is a sensor that measures triaxial acceleration and triaxial angular velocity. The inertial measurement unit 1306 includes an accelerometer, which can output linear acceleration signals on three axes in space, and a gyroscope, which can output angular velocity signals on three axes in space. In an exemplary embodiment, the inertial measurement unit 1306 is coupled via at least one or more notches 1118 present on the second end 1106 of the cylindrical element 1102. The inertial measurement unit 1306 is an inertial sensor or an acoustic sensor. Further, the inertial measurement unit 1306 can include an accelerometer, a NEMS gyrometer, or a gyroscope. The inertial measurement unit 1306 can include a rechargeable battery or any other power source (not shown).

Figure 2A:
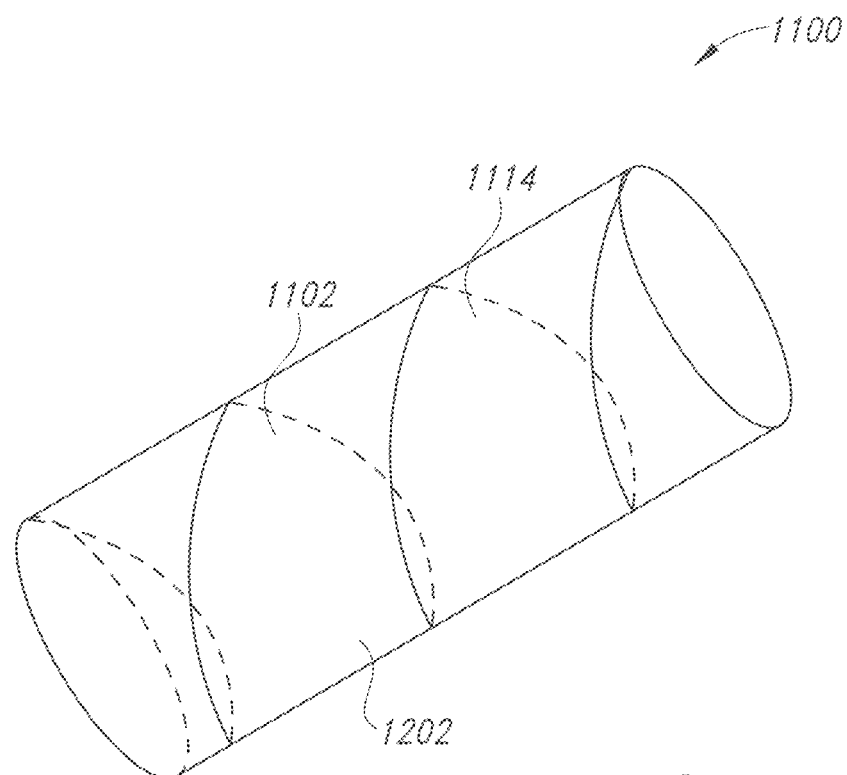
FIG. 2A-2B is a schematic diagram of various radio-opaque wire configurations of the cylindrical element of the present invention.
Figure 2B:
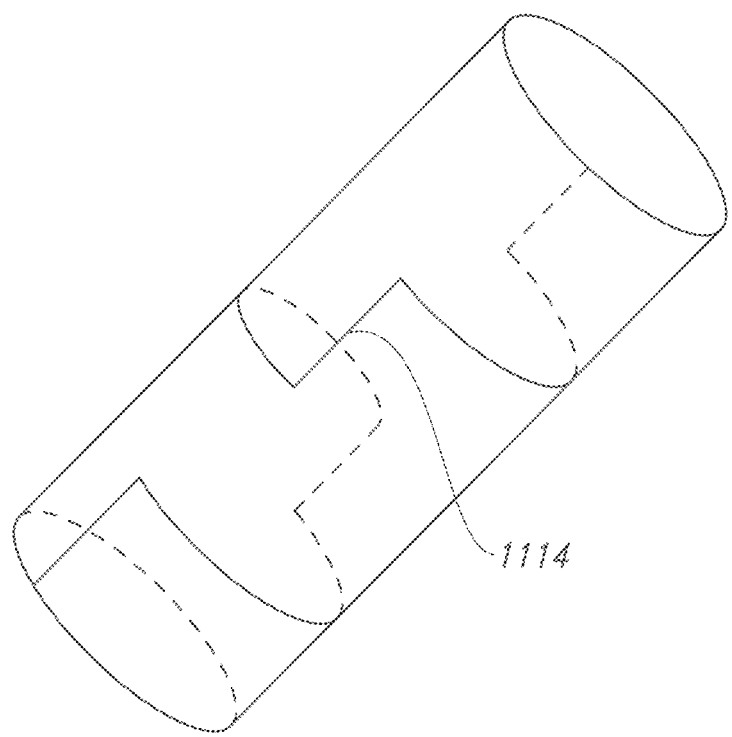

FIG. 2A-2B is a schematic diagram of various radio-opaque patterns that can be achieved using different wire configurations on the cylindrical element 1102. The radio-opaque wire 1114 is enabled to attach along a surface area of the cylindrical element 1102 as a helical wire (FIG. 2A) or a segmented wire (FIG. 2B). The helical wire or a segment wire enables the surgeon and the tracking system to distinguish between different cylindrical elements present in the fluoroscopic image and to estimate their pose. The helical wire (FIG. 2A) or a segmented wire (FIG. 2B) provide distinct radio-opaque patterns that are detectable in a fluoroscopic image.

FIG. 3A is a schematic diagram showing the three-dimensional dual fiducial-sensor trackable device 1100 of this invention. The three-dimensional dual fiducial-sensor trackable device 1100 is attached or temporarily (during the fluoroscopic image) statically fixed to the patient's body 1304. The three-dimensional dual fiducial-sensor trackable device 1100 includes a cylindrical element 1102, and an inertial measurement unit 1306. The cylindrical element 1102 holds the K-wire 1308 in the hollow slot 1112 of the cylindrical element 1102. In one example, a handle 1310 is coupled to the second end 1106 of the cylindrical element 1102 via at least one or more notches 1118 present on the second end 1106 of the cylindrical element 1102. The handle 1310 is connected to the inertial measurement unit 1306 which includes or is coupled to a transmission unit 1307. The transmission unit 1307 transmits a signal to computer device 1410. The handle 1310 can be of various shapes and sizes and should be long enough so that the surgeon's hand is not exposed during capturing of the fluoroscopic image of the patient 1304.

Now referring to FIGS. 3B-3C, the hollow slot 1112 of the cylindrical element 1102 enables attachment of a surgical instrument (i.e., surgical device) 1314 to the three-dimensional dual fiducial-sensor trackable device 1100 via a rod 1312. The rod 1312 is attached to the surgical instrument 1314. The rod 1312 can be placed longitudinally (bottom) or transversely (top) to the surgical instrument 1314 (i.e., cup impactor). In an alternate embodiment, during orthopedic surgery, a surgeon needs to view the real-time position of the K-wire and its potential trajectory with reference to the fluoroscopic image. The surgeon can place the K-wire in the hollow slot 1112 of the cylindrical element 1102 of the three-dimensional dual fiducial-sensor trackable device 1100. The surgeon is enabled to place the cylindrical element of the three-dimensional dual fiducial-sensor trackable device in contact with a patient's bone, soft tissue, or skin.

Figure 4:
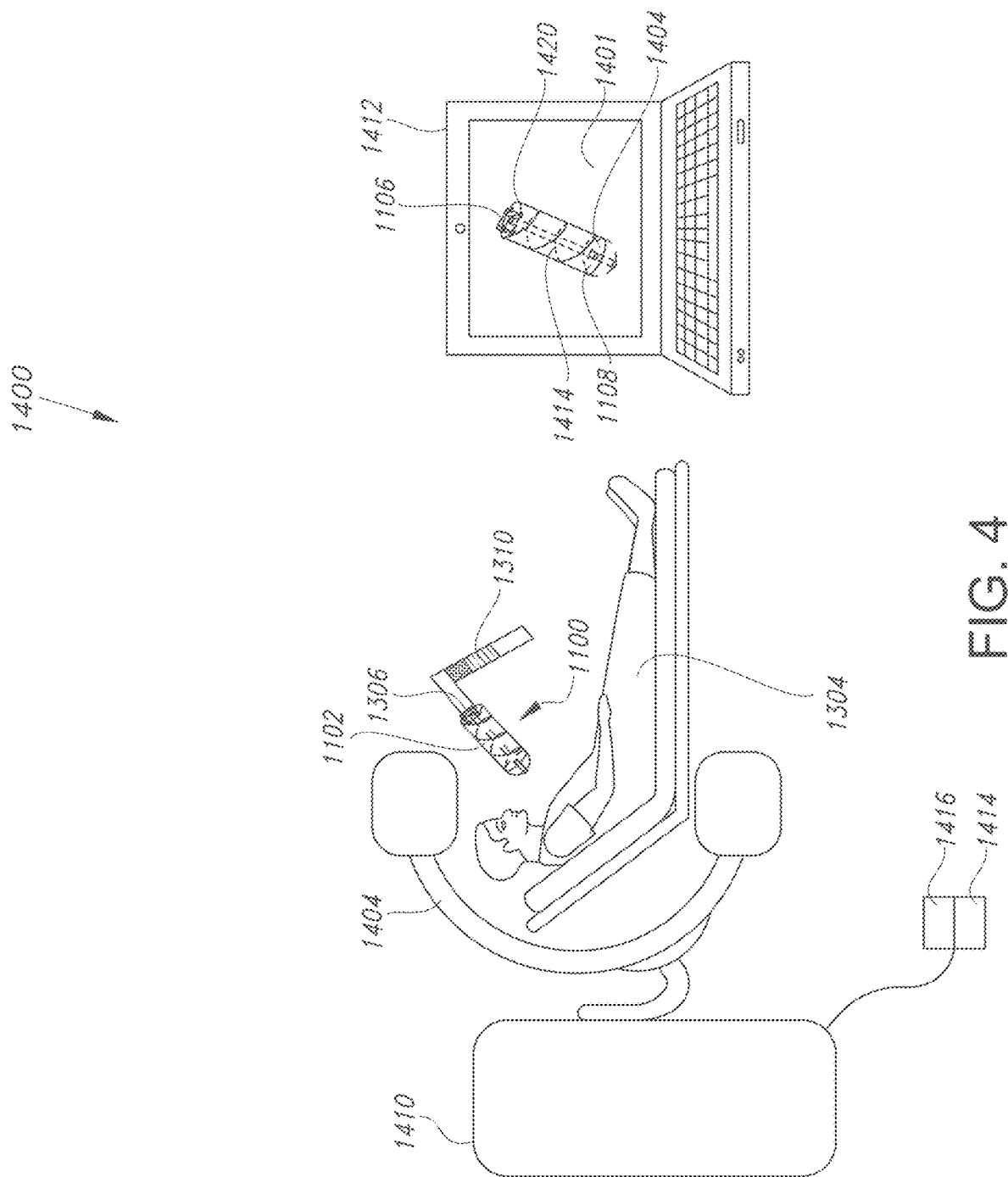
FIG. 4 is a schematic diagram showing the interaction of the three-dimensional dual fiducial-sensor trackable device and the surgical device of a system of the present invention

FIG. 4 is a schematic diagram showing the interaction of the three-dimensional dual fiducial-sensor trackable device 1100 and the surgical device of a system 1400 of the present invention. A fluoroscopic image 1401 of patient 1304 is captured by a C-arm 1404 (i.e., an imaging device) during intraoperative use of the three-dimensional dual fiducial-sensor trackable device 1100. The cylindrical element 1102 is visible in the captured fluoroscopic image as a three-dimensional mesh or three-dimensional grid form or as a set of circles. Some elements (1106, 1108, 1114) of cylindrical element 1102 are radio opaque. The C-arm 1404 is configured to transmit the captured fluoroscopic image to a computing device 1410 which includes or is in electronic communication with a display unit 1412 a processing unit 1414 and a memory 1416. The display unit 1412 can be a laptop, PDA, mobile device, or desktop system. Further, the inertial measurement unit 1306 of the three-dimensional dual fiducial-sensor trackable device 1100 is configured to transmit its position data to the processing unit via a transmission unit (i.e., a wireless network such as Wi-Fi, Bluetooth, RF443 Mhz, or any other wired or wireless network). The positional data can be three-dimensional positioning data i.e., x, y, z coordinates or angles of the inertial measurement unit 1306.

The system 1400 include a processing unit 1414 configured to (a) determine the cylindrical element 1102 position (i.e., two-dimensional position) or orientation with reference to a patient anatomical structure through the first radio-opaque disk 1108, the second radio-opaque disk 1110, and the radio opaque wire 1114 of the cylindrical element 1102, (b) overlaying the position of the cylindrical element 1102 with reference to the position data of the inertial measurement unit 1306 to determine the real time position of the cylindrical element 1102 in the fluoroscopic image (c) determine the position of the surgical device with reference to the real time position of the cylindrical element 1102 and (d) display a real-time graphical representation 1420 of the cylindrical element 1102 (i.e., dual part) and the radio-opaque wire 1114 such as a K-wire (and is projected potential trajectory) on the fluoroscopic image relative to the surgical device on a display unit 1412. The surgical device system 1400 is configured to update the position of the cylindrical element 1102 to display the new position of the radio-opaque wire 1114 (K-wire) and its trajectory on the fluoroscopic image using new position data of the inertial measurement unit 1306 obtained over the time.

Figure 5:
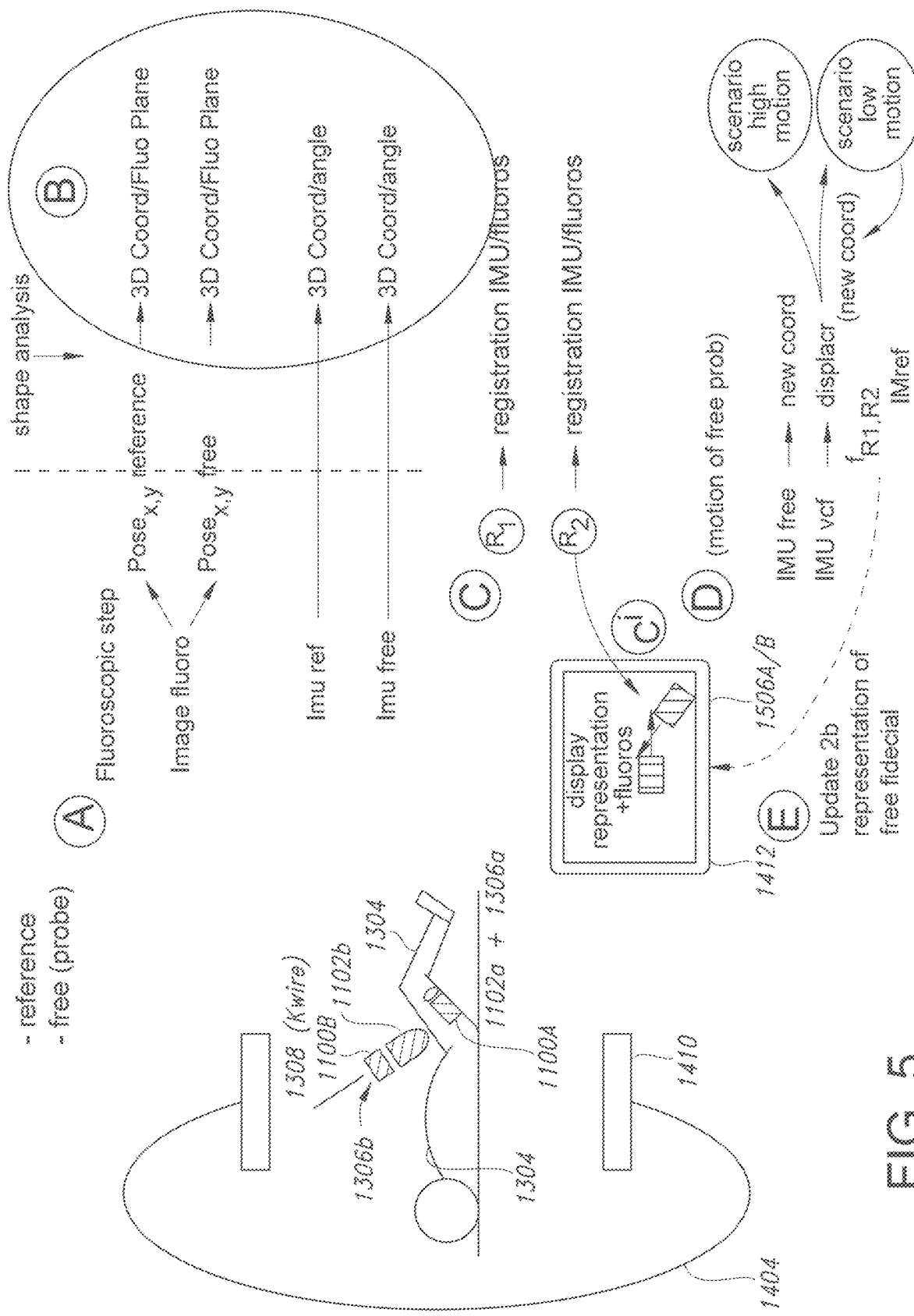
FIG. 5 is a schematic diagram of the process using a plurality of three-dimensional dual fiducial-sensor trackable devices.

Now referring to FIG. 5, a schematic diagram of the process is shown. In this embodiment, a plurality of three-dimensional dual fiducial-sensor trackable devices 1100 are used simultaneously. These three-dimensional dual fiducial-sensor trackable device 1100 can be distinguished in fluoroscopic images with different geometry configurations for radiopaque wires 1114 (e.g., FIG. 2). The inertial sensors send positions and angles with their unique identification system. In this configuration, a first three-dimensional dual fiducial-sensor trackable device 1100A is attached to the patient's body (1102a+1360a) and the second three-dimensional dual fiducial-sensor trackable device 1100B (1102b+13606b) is free to be moved to another section of the patient body. The first three-dimensional dual fiducial-sensor trackable device attached to the patient is the reference three-dimensional dual fiducial-sensor trackable device. Its role will be to detect any displacement of the patient's body 1304 part since the last fluoroscopy acquisition.

The process to use a plurality of three-dimensional dual fiducial-sensor trackable devices 1100 is as follows: Step A: a fluoroscopy is acquired with at least two three-dimensional dual fiducial-sensor trackable devices 1100 within the acquisition field. As described above, the three-dimensional dual trackable devices 1100 with respect to the fluoroscopy plane is estimated from the images (step B). With the registration of the inertial measurement unit coordinates during the fluoroscopy, it is possible to calculate the geometrical transformation (registration) which allows to pass from one referential to the other (step C). A virtual model in the fluoroscopy image (step C') is rendered. If the surgeon moves the second three-dimensional dual fiducial-sensor trackable device 1100B (1102b+13606b), a new representation considers the body displacement based on the reference inertial measurement unit (D) to display on the screen (E) 1412.

In the case of displacement detection from the reference inertial measurement unit two scenarios can be realized. The selection of one or the other scenario will depend on the surgery applied. The first scenario "Important Motion" alerts the patient that an important displacement has been detected and that the system is no longer able to predict positions with accuracy. It is necessary to repeat a fluoroscopy acquisition to reset the tracking system to nominal conditions. A second embodiment corresponds to a "small displacement" in this case the rendering/navigation system considers this displacement by displaying the position of the "free dual" second three-dimensional dual fiducial-sensor trackable device 1100B (1102b+13606) with respect to the "reference dual" first three-dimensional dual fiducial-sensor trackable device 1100A (1102a+1360a) position. The navigation system can also decide that a succession of small displacements can by accumulated errors generate too much risk of error in this case the "Large displacement" scenario is triggered. At each new fluoroscopy acquisition, the system switches to the nominal state since the three-dimensional dual fiducial-sensor trackable device positions (two-dimensional and three-dimensional) are reset/stimulated.

The use of a three-dimensional dual fiducial-sensor trackable device is shown. This illustrative embodiment shows the three-dimensional dual fiducial-sensor trackable device 1100 as a guidance for a K-wire 1308 to determine a trajectory of the K-wire 1308 during orthopedic surgery. The three-dimensional dual fiducial-sensor trackable device 1100 (i.e., dual part) is attached to the patient's body 1304 as shown in image 1506. The surgeon is enabled to capture an anterior-posterior (AP) and lateral images of the patient's body 1502 using an imaging device (i.e., C-arm head). The inertial measurement unit of the three-dimensional dual fiducial-sensor trackable device is configured to determine displacements of the K-wire 1308 during the capture of the anterior-posterior (AP) and lateral images of the patient's body 1304. The imaging device is configured to transmit the anterior-posterior (AP) and lateral images to a processing unit. The inertial measurement unit is configured to transmit its position or orientation to the processing unit. The processing unit is configured to calibrate the position of the inertial measurement unit with reference to the cylindrical element 1102 detected in the anterior-posterior (AP) and lateral images of the patient's body 1304. Further, the display unit is configured to display the anterior-posterior (AP) 1506a and lateral fluoroscopic image 1506b and the trajectory of the K-wire 1508a, 1508b with reference to the cylindrical element 1102 computed through the calibration step. The surgeon is enabled to provide input in response to the displayed trajectory 1508a, 1508b of the K-wire (i.e., whether the trajectory of the K-wire overlaps with the K-wire visible in the fluoroscopic image 1506a, 1506b). The input is Yes, the calibration is correct or no, the calibration is not correct. As the surgeon moves the cylindrical element, the processing unit recomputes the positional data of the inertial movement unit with reference to the cylindrical element 1102, and the rendering of the K-wire is updated in real time in the anterior-posterior (AP) and lateral fluoroscopic image i.e., (new trajectory of K-wire is displayed on the display unit).

Figure 6:
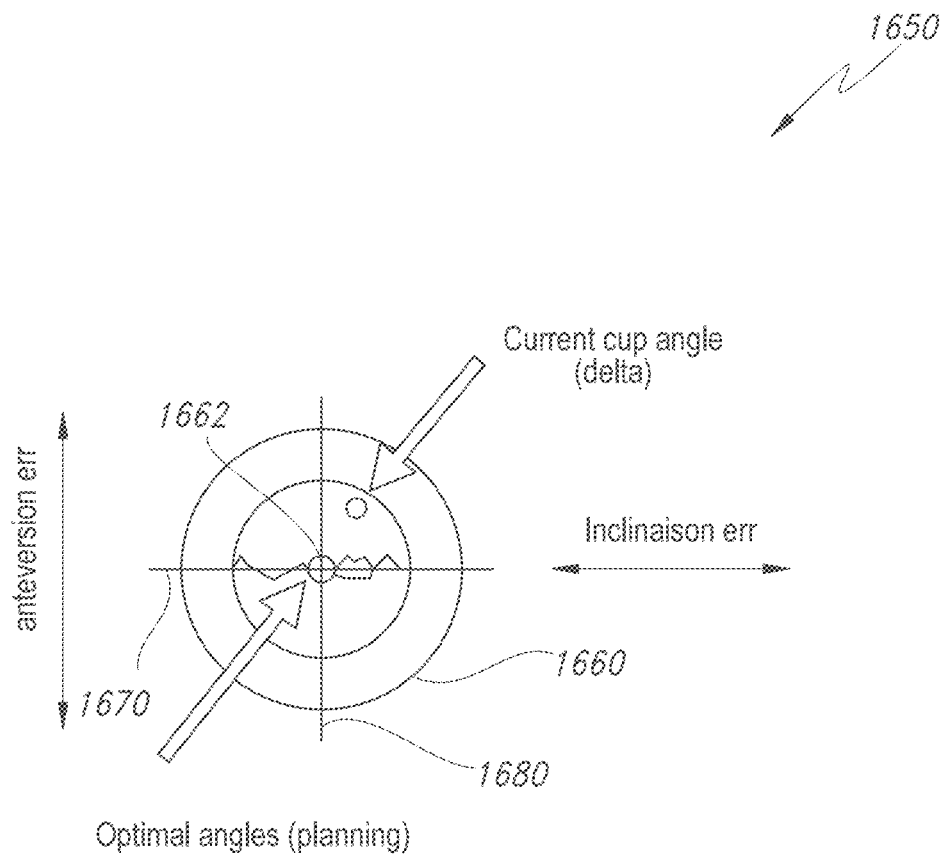
FIG. 6 is an illustration of an optimal angle planning widget.

Now referring to FIG. 6 a graphical widget 1650 can also be made available on the computer screen to render the differences in "current" vs "target" angles. This widget represents a series of concentric circles 1660, the common center of these circles 1662 represents the optimal angles to be reached. The concentric circles represent variations of angles of 5 degrees. The current angles of the cup (transmitted by the inertial measurement unit and the transmission unit) are represented by a moving point in this widget. The surgeon places the cup optimally and must place this point in the center of the widget. The choice of the horizontal X 1670 and vertical Y 1680 are chosen so that the surgeon's movement is natural and intuitive.

EXAMPLES

To surgically repair fractures, surgeons may use implants, for example plates and screws. Fixing the plates to the bone requires surgeons to place screws in the plate. To do this, they have to make an incision in the skin to insert the screw. To estimate the position of the incision, the user relies on one or more fluoroscopic images to ensure the correct alignment of their incision and a hole in the plate to receive the screw. This procedure increases the mental load on the surgeon and slows down the surgical procedure workflow while increasing the radiation dose. The use of the device and the knowledge of the geometric model of the plate allows for considerable simplification to this aspect of the procedure. For example, in hip nailing, the placement of the distal screw is not easy because of the length of the implant and rotation of the distal end of the bone relative to the nail which may have rotated inside the bone.

Figure 7A:
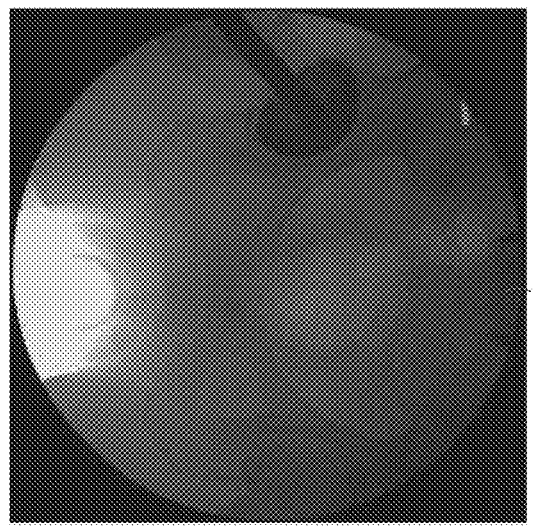
Figure 7B:
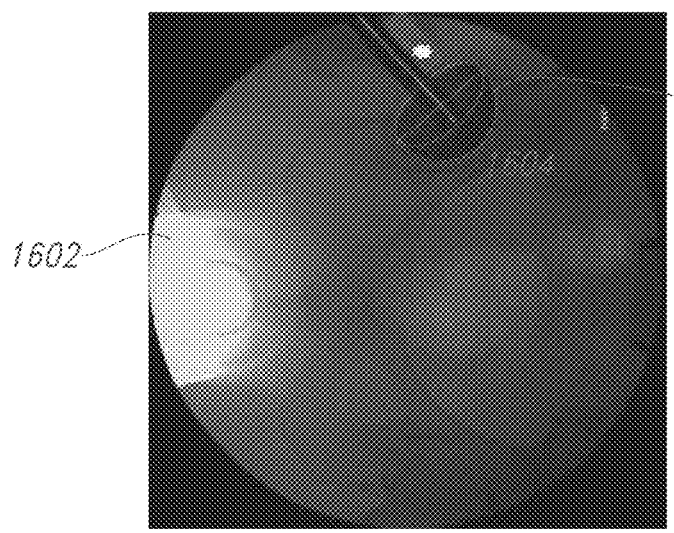
Figure 7B:
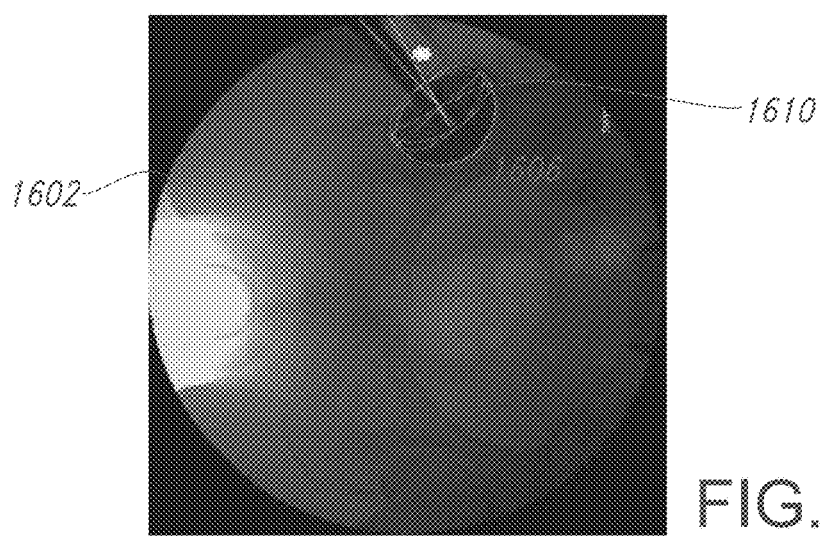

Now referring to FIG. 7A-C, 7A provides an illustrative embodiment showing the three-dimensional dual fiducial-sensor trackable device 1100 coupled to a cup impactor 1610. The cup impactor 1610 is placed by the surgeon at a particular angle in order to maintain the patient's leg mobility. The three-dimensional dual fiducial-sensor trackable device 1100 is fixed longitudinally on the cup impactor 1610. The surgeon is enabled to place the cup impactor 1610 into an acetabulum. A fluoroscopic image of the acetabulum is captured using the imaging device (C-arm). The fluoroscopic image 1602 shows the three-dimensional dual fiducial-sensor trackable device coupled to a cup impactor 1610. The fluoroscopic image is transmitted to the processing unit. The processing unit determines a position of the three-dimensional dual fiducial-sensor trackable device 1100 and the cup impactor 1610 with reference to the patient's acetabulum via the cylindrical element of the three-dimensional dual fiducial-sensor trackable device. The inertial measurement unit of the three-dimensional dual fiducial-sensor trackable device 1100 transmits its three-dimensional position data to the processing unit. The processing unit computes/overlays the position of the three-dimensional dual trackable device 1100 and the cup impactor 1610 with reference to the three-dimensional position data of the inertial measurement unit to determine or estimate the real time three-dimensional position of the three-dimensional dual trackable device 1100 and the cup impactor 1610 with reference to the patient's acetabulum.

Now referring to FIG. 7B-7C a visual rendering 1604 (i.e., wireframe representation of a half-sphere in blue color) of the estimated real-time three-dimensional position is superimposed on the fluoroscopic image as shown in the display unit. An analysis of the curvature/half-radius of the cup portion of the cup impactor 1610 provides the spatial dimension (mm/pixel). The surgeon is enabled to provide an input on whether the superimposed position of the wireframe representation and the estimated real time three-dimensional position of the three-dimensional dual fiducial-sensor trackable device 1100 and the cup impactor 1610 coincides. Further, to represent the position of the cup impactor 1610 another wireframe half sphere representation is rendered with a different color (green) 1606.

The inertial measurement unit continuously transmits its three-dimensional position data to the processing unit, the wireframe representation of a half sphere in blue color 1604 is updated in real time with reference to the current position of the cup impactor 1610. This approach allows optimal and quantified positioning and avoids the acquisition of additional images to estimate the correct positioning of the cup impactor 1610 into, for example an acetabulum.

Figure 8A:
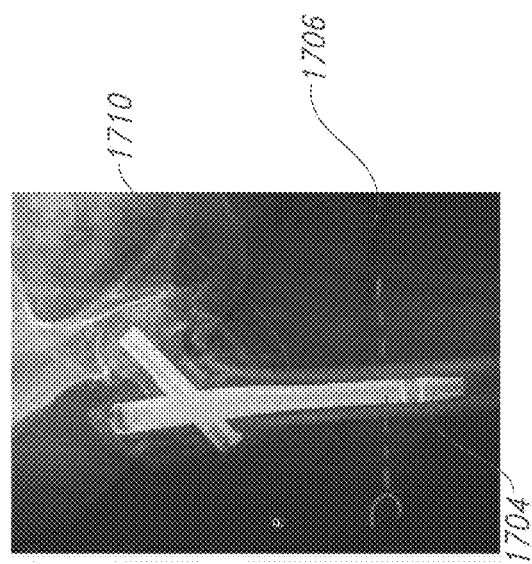
FIG. 8A-8C is an illustrative embodiment showing the three-dimensional dual fiducial-sensor trackable device coupled to a nail.
Figure 8B:
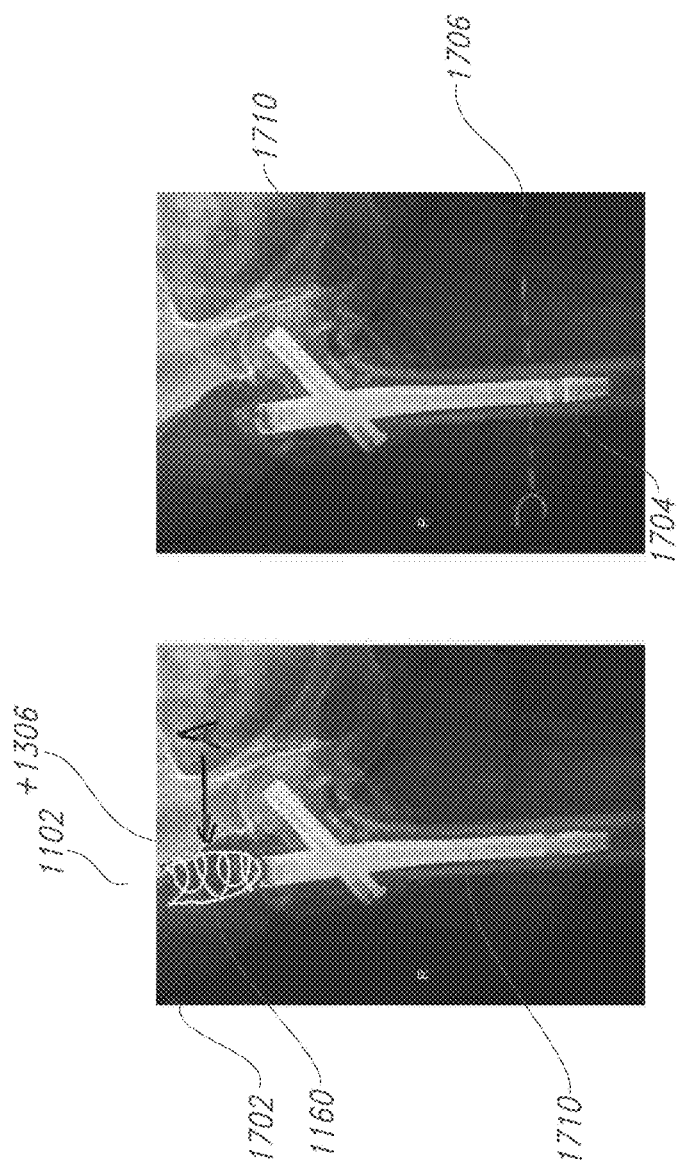
Figure 8C:
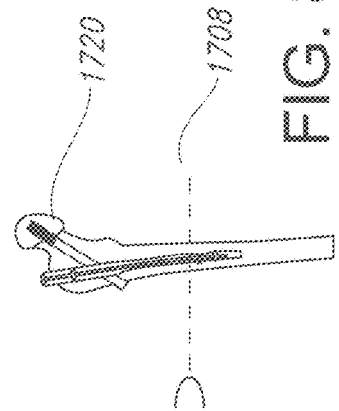

Now referring to FIG. 8A-8C, to surgically repair fractures, surgeons may use implants, for example nails and screws. Fixing the nail to the bone requires surgeons to place screws through the nail and into the bone. To do this, they have to make an incision in the skin to insert the screw. To estimate the position of the incision, the surgeon relies on one or more fluoroscopic images to ensure the correct alignment of their incision and a hole in the nail to receive the screw. The surgeon then estimates the angle and depth position of the screw relative to the anatomy. This procedure increases the mental load on the surgeon and slows down the surgical procedure workflow while increasing the radiation dose. The use of the three-dimensional dual fiducial-sensor trackable 1102 and the knowledge of the geometric model of the nail allows for considerable simplification to this aspect of the procedure. For example, in hip nailing, the placement of the distal screw is not easy because of the length of the implant and rotation of the distal end of the bone relative to the nail which may have rotated inside the bone.

For example, for each fluoroscopic image 1701, the system updates the registration computation by detecting the pose of the three-dimensional dual fiducial-sensor trackable device 1100 which is attached to a nail 1710 (FIG. 8A). In FIG. 8B, the surgeon fixes the distal nail using a screw in a manufactured hole in the nail 1710. The navigation system detects the hole and displays the fluoroscopic image with the two yellow bars 1740. The surgeon uses the navigation system in the fixation of the screw 1706 which is represented by the virtual trajectory of the fiducial provided by the inertial measurement unit 1306.

In FIG. 8C, a virtual reality view of a three-dimensional model 1708 of the nail and the virtual trajectory of the fiducial are shown. It is a free view mode display on the control screen. The surgeon can freely update the view angle to better appreciate the trajectory. This view is updated in real time according to positions sent by the inertial measurement unit 1306.

FIGS. 9A-9E provides an illustration of the use of the 1100 for treatment of a spine for pedicel screw placement or needle guidance. Preoperative planning using plain radiographs and CT scan is important in deciding the bone quality, pedicle transverse diameter and screw trajectory. Here a pedicle screw 1900 is attached to a three-dimensional dual tracking device 1100. After decorticating the pedicle entry site with a burr and penetrating the site with an awl, a curved or straight pedicle probe is used to develop a path. After cannulation and confirmation of the pedicle as well as the appropriate trajectory, the largest possible pedicle screw is placed for the screw through the cancellous bone of the pedicle into the vertebral body. FIGS. 9A-E shows the same sequence as FIG. 11. FIG. 9B is a CT image showing orientation and direction of pathway of the screw. FIG. 9A is the pre or intraoperative radiographic image with arrows showing screw/implant trajectory pathways and projections for implant/screw 1900 and the three-dimensional dual fiducial-sensor trackable device 1100. FIGS. 9C, 9D, and 9E are the three different three-dimensional views associated with the two-dimensional view with the arrows once again showing the implant trajectory projected pathway.

Figures 10A, 10B:
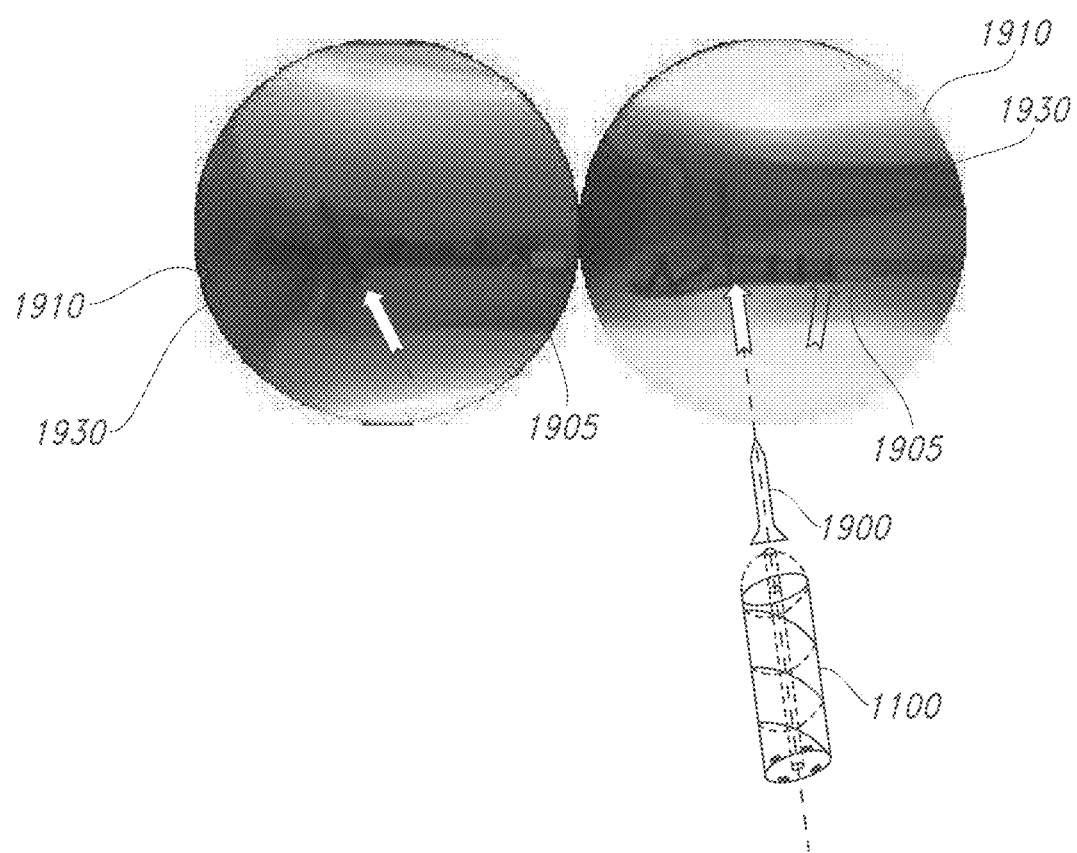
FIG. 10A-10B is an illustration of the use of the present device for treatment of an ankle trauma using plate and screw.

Now referring to FIG. 10A-10B an illustration of the use of the present device for treatment of a fracture such as an ankle using a plate and screws is shown. Fixing the plates 1920 to the bone 1930 requires surgeons to place screws in the plates. To do this, they have to make an incision in the skin to insert the screw. To estimate the position of the incision 1905, the surgeon relies on one or more fluoroscopic images 1910 to ensure the correct alignment of their incision and a hole in the plate 1920 to receive the screw 1900. This procedure increases the mental load on the surgeon and slows down the surgical procedure workflow while increasing the radiation dose. The use of the device and the knowledge of the geometric model of the plate allows for considerable simplification to this aspect of the procedure. For example, in bone fractures, the placement of the screw 1900 is not easy because of the bone size, orientation and relative position to the implant, which can move in real time during reduction of the fracture or fixation of the implant. In an alternate embodiment, at each fluoroscopy, the system updates the registration computation by detecting the pose of the plate 1920 and screw 1900 and correlating it to the current Inertial Measurement Unit 1306 coordinate.

Figure 11A:
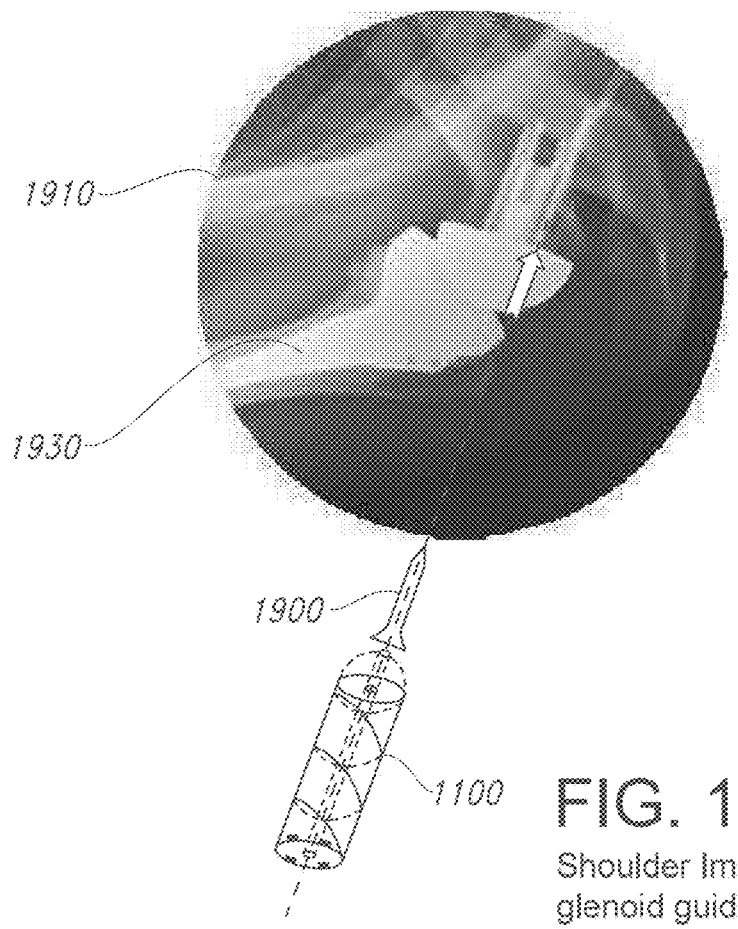
FIG. 11A-11B is an illustration of the use of the present device for a shoulder implant in a glenoid guidance.
Figure 11B:
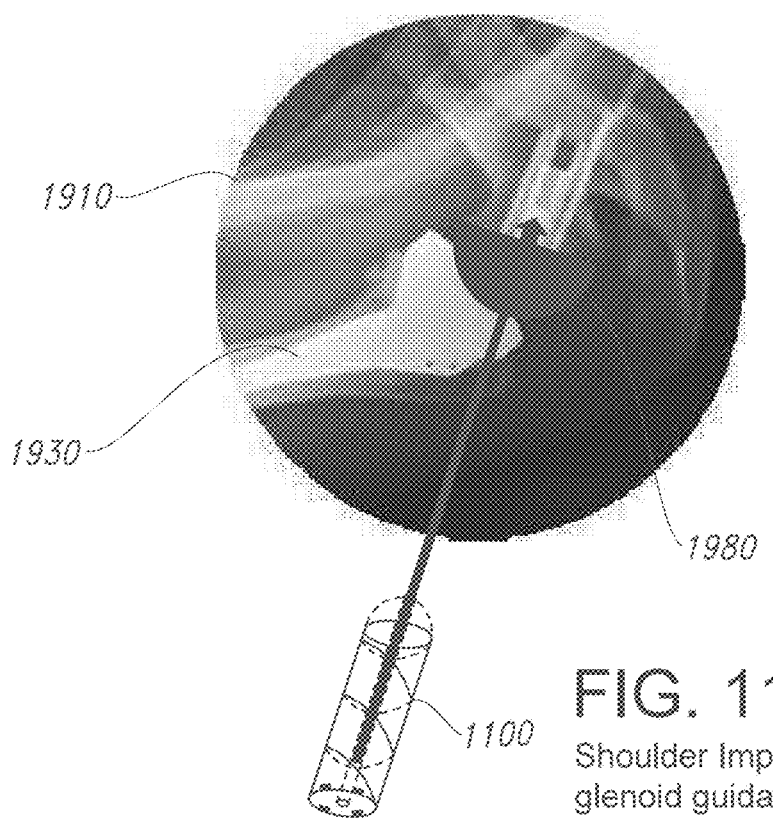

Now referring to FIG. 11A-11B an illustration of the use of the present device for glenoid guidance of a shoulder implant 1980 is shown. Fixing the implant 1980, such as a glenoid component, to the bone 1930 requires surgeons to place screws 1900 in the implant 1980. To do this, they have to project pathways of screws into the bone. To estimate the position of the implant, the user relies on one or more fluoroscopic images to ensure the correct alignment and orientation of their implant 1980 and a hole in the plate to receive the screw and the bone receiving the screw 1900. This procedure increases the mental load on the surgeon and slows down the surgical procedure workflow while increasing the radiation dose. The use of the three-dimensional dual fiducial-sensor trackable device 1100 for and the knowledge of the geometric model of the implant 1980 allows for considerable simplification to this aspect of the procedure. For example, in shoulder surgery, the placement of the screw 1900 is not easy because of the bone size, orientation and relative position to the implant, which can move in real time during guidance of the screw and fixation of the implant.

In an alternate embodiment, at each fluoroscopy, the system updates the registration computation by detecting the pose of the implant and screw element and correlates it to the current Inertial Measurement Unit 1306 coordinate.

Now referring to FIG. 12A-12C an illustration of the use of the present device for a knee implant using cutting guides 2010 and block element 2020 is shown. Fixing the knee implant, such as a femoral or tibial component, to the bone requires surgeons to place these implants in specific positions on the bone. To do this, they have to project pathways of implant orientation relative to the bone. To guide the position of the implant, the user relies on one or more fluoroscopic images to ensure the correct alignment and orientation of their cutting blocks 2010 or guides 2020. This procedure increases the mental load on the surgeon and slows down the surgical procedure workflow while increasing the radiation dose. The use of the three-dimensional dual fiducial-sensor trackable device 1100 and the knowledge of the geometric model of the implant allows for considerable simplification to this aspect of the procedure. For example, in knee surgery, the placement of the blocks 2020 is not easy because of the bone size, orientation and relative position to the bone, which can move in real time during guidance of the block and fixation of the blocks to the bone. Cuts are made through the blocks 2020 which then define the orientation and position of the implant 1980. In an alternate embodiment, at each fluoroscopy, the system updates the registration computation by detecting the pose of the implant 1980 and block element 2020 and correlates it to the current inertial Measurement Unit 1306 coordinate.

Figure 13:
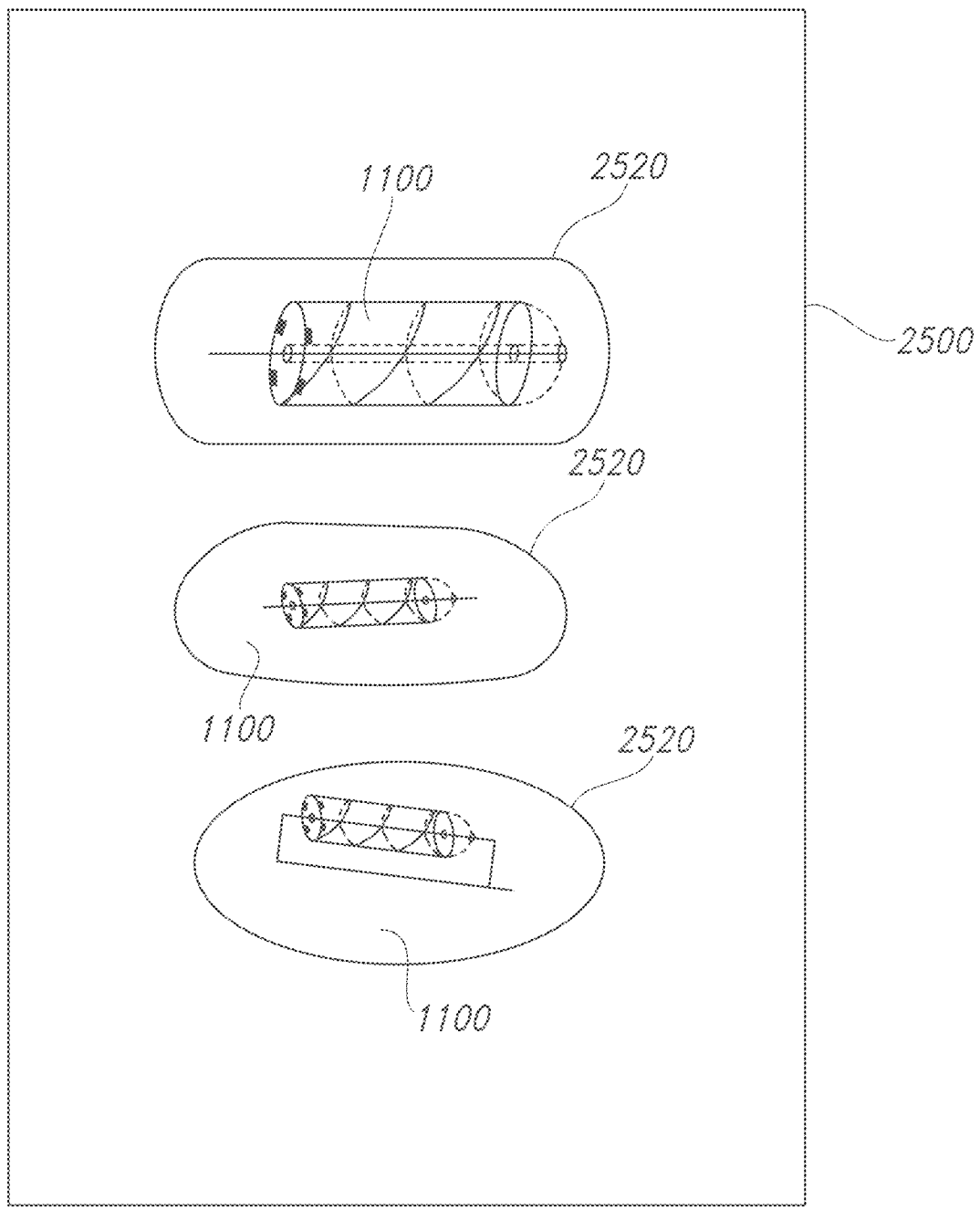
FIG. 13 is an illustration of an exemplary embodiment of a kit.

FIG. 13 shows an exemplary embodiment of kit 2500. The kit 2500 includes A three-dimensional dual fiducial-sensor trackable device comprising: an element having a first end and a second end, wherein the first end comprises a first radio-opaque disk disposed therein, wherein the second end comprises a second radio-opaque disk disposed therein, wherein the first radio-opaque disk and the second radio-opaque disk are configured to determine a dimensional position of the element in a fluoroscopic image; wherein the element is comprised of a hollow slot in between the first end and the second end; wherein the element includes a radio-opaque wire attached along a surface area of the element; wherein the radio-opaque wire is configured to determine a pose, or a position of the element in the fluoroscopic image; and an inertial measurement unit, coupled to the second end of the element, configured to transmit one or more parameters to a display unit through a wireless network, wherein the one or more parameters are selected from the group consisting of: a position, an angle, acceleration, and x, y, z coordinates of the inertial measurement unit and a container 2520 to sterilely receive each of the plurality of three-dimensional dual fiducial-sensor trackable devices.

While the invention has been described with reference to preferred and example embodiments, it will be understood by those skilled in the art that a variety of modifications, additions, and deletions are within the scope of the invention, as defined by the following claims.

The invention claimed is:

1. A three-dimensional dual fiducial-sensor trackable device comprising:
an element having a first end and a second end, wherein the first end comprises a first radio-opaque disk disposed therein, wherein the second end comprises a second radio-opaque disk disposed therein, wherein the first radio-opaque disk and the second radio-opaque disk are configured to determine a dimensional position of the element in a fluoroscopic image; wherein the element is comprised of a hollow slot in between the first end and the second end; wherein the element comprises a radio-opaque wire attached along a surface area of the element; wherein the radio-opaque wire is configured to determine a pose, or a position of the element in the fluoroscopic image; and an inertial measurement unit, coupled to the second end of the element, configured to transmit one or more parameters to a display unit through a wireless network, wherein the one or more parameters are selected from the group consisting of: a position, an angle, acceleration, and x, y, z coordinates of the inertial measurement unit.

2. The three-dimensional dual fiducial-sensor trackable device of claim 1, wherein the first end is comprised of a round-shaped end configured to rotate the element, when the element is in contact with a patient's bone or a patient's skin.

3. The three-dimensional dual fiducial-sensor trackable device of claim 1, wherein the radio-opaque wire is of a helical configuration.

4. The three-dimensional dual trackable device of claim 1, wherein the radio-opaque wire is of a segmented configuration.

5. The three-dimensional dual fiducial-sensor trackable device of claim 1, wherein the hollow slot is configured to receive a surgical element and the surgical element is selected from the group consisting of: a K-wire, a guide wire, a fixation rod, a drill bit, a screw, and a surgical device.

6. The three-dimensional dual fiducial-sensor trackable device of claim 1, wherein the inertial measurement unit is selected from the group consisting of: an accelerometer, a NEMS gyrometer, and a gyroscope.

7. The three-dimensional dual fiducial-sensor trackable device of claim 1, further comprising a: package configured to receive at least one of the three-dimensional dual fiducial-sensor trackable device and the sterile container for the three-dimensional dual fiducial-sensor trackable device.

8. A method for intra-operative use of an at least one three-dimensional dual fiducial-sensor trackable device for intraoperative navigating a surgical device or anatomical structure, the method comprising the steps of:
   placing the at least one three-dimensional dual fiducial-sensor trackable device on to a portion of patient's anatomy, or attaching the device to an instrument, an implant, or an imaging device, wherein each of the at least one three-dimensional dual fiducial-sensor trackable device is comprised of a distinct radio-opaque pattern and an inertial measurement unit;
   capturing a fluoroscopic image of the patient's anatomy using an imaging device;
   intraoperatively determining a first positioning data of the distinct radio-opaque pattern on the fluoroscopic image;
   obtaining a second positioning data of the inertial measurement unit;
   overlaying the first positioning data and the second positioning data of the inertial measurement unit to determine a real time position of the patient anatomy, the instrument, the implant, or the imaging device in the fluoroscopic image;
   determining a position of the portion of the patient anatomy, the instrument, the implant, or the imaging device, with reference to the real time position of the least one three-dimensional dual fiducial-sensor trackable device; and
   displaying a real time graphical representation of the least one three-dimensional dual fiducial-sensor trackable device on the fluoroscopic image relative to the portion of the patient anatomy, the instrument, the implant, or the imaging device.

9. The method of claim 8, further comprising the step of: intra-operatively navigating the surgical device with reference to a real time graphical representation of the at least one three-dimensional dual fiducial-sensor trackable device.

10. The method of claim 8, wherein the surgical device is at least one of the but not limited to a K-wire, fixation rod, or cup impactor.

11. The method of claim 8, wherein the positioning data of the distinct radio-opaque pattern is position and orientation of the distinct radio-opaque pattern in the fluoroscopic image with reference to the patient's anatomy.

12. The method of claim 8, wherein the positioning data of the inertial measurement unit is a position, x, y, and z coordinates, angle, or orientation of the inertial measurement unit.

13. The method of claim 8, wherein overlaying the positioning data of the distinct radio-opaque pattern and the positioning data of the inertial measurement unit to determine real time position of the distinct radio-opaque pattern on the fluoroscopic image comprising the step of: overlaying a two-dimensional positioning data of the distinct radio-opaque pattern and a three-dimensional positioning data of the inertial measurement unit on the fluoroscopic image.

14. The method of claim 8, wherein the inertial measurement unit comprises an accelerometer, a NEMS gyrometer, and a gyroscope.

15. The method of claim 8, wherein the least one three-dimensional dual fiducial-sensor trackable device is comprised of a first three-dimensional dual fiducial-sensor trackable device comprised of a first radio-opaque wire configuration and a second three-dimensional dual trackable fiducial-sensor device, comprised of a second radio-opaque wire configuration, wherein the first radio-opaque wire configuration and the second radio-opaque wire configuration are distinguishable in the fluoroscopic image.

16. The method of claim 15, wherein the first three-dimensional dual fiducial-sensor trackable device is attached to the patient and further comprising the step of moving the second three-dimensional dual trackable device, whereby a virtual image is generated based on a reference inertial measurement unit of the first three-dimensional dual fiducial-sensor trackable device.

17. The method of claim 8 further comprising generating a graphical display showing an X and Y axis surrounded by a series of concentric circles and a common center showing an optimal angles to be reached by a surgical process;
   transmitting data from the inertial measurement unit and the transmission unit;
      showing a current angles of a cup as a moving point on said display; and
   surgically moving the cup until it reached the common center of the graphical display.

18. The method of claim 8, wherein the surgical device is an implant, and the steps further comprise: superimposing a representation of the implant with an estimated three-dimensional position of the implant.

19. The method of claim 8, wherein the anatomical structure is a spine, and the steps further comprise: visually showing a virtual trajectory of a screw or nail.

* * * * *

UNITED STATES PATENT AND TRADEMARK OFFICE
CERTIFICATE OF CORRECTION

PATENT NO. : 12,376,913 B2
APPLICATION NO. : 18/139471
DATED : August 5, 2025
INVENTOR(S) : Boddington et al.

Page 1 of 1

It is certified that error appears in the above-identified patent and that said Letters Patent is hereby corrected as shown below:

In the Claims

In Column 13, Line 11, Claim 4, after "dual", insert --fiducial-sensor--

In Column 13, Line 24, Claim 7, delete "a:" and insert --a-- therefor

In Column 13, Line 53, Claim 8, after "the", insert --at--

In Column 13, Line 56, Claim 8, after "the", insert --at--

In Column 14, Line 27, Claim 15, after "the", insert --at--

Signed and Sealed this
Twenty-eighth Day of October, 2025

John A. Squires
*Director of the United States Patent and Trademark Office*